US00PP31822P3

(12) United States Plant Patent
Brazelton et al.

(10) Patent No.: US PP31,822 P3
(45) Date of Patent: Jun. 2, 2020

(54) BLUEBERRY PLANT NAMED 'FC13-122'

(50) Latin Name: *Vaccinium corymbosum*
Varietal Denomination: FC13-122

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Hilo, HI (US)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 16/350,780

(22) Filed: Jan. 10, 2019

(65) Prior Publication Data

US 2019/0215999 P1 Jul. 11, 2019

Related U.S. Application Data

(60) Provisional application No. 62/709,364, filed on Jan. 11, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

*Primary Examiner* — Kent L Bell

(57) ABSTRACT

The new blueberry plant variety 'FC13-122' is provided. 'FC13-122' is a commercial variety intended for the hand harvest fresh fruit market. The variety is produced from a cross of 'ZF06-050' (female parent, not patented) and 'ZF06-013' (male parent, not patented), which can be distinguished by its outstanding features.

6 Drawing Sheets

Latin name of the genus and species: Genus—*Vaccinium*. Species—*corymbosum*.

Variety denomination: The new blueberry plant claimed is of the variety denominated 'FC13-122'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L. hybrid) plant, referred to as 'FC13-122', as herein described and illustrated. The new blueberry plant variety 'FC13-122' is a commercial variety intended for the hand harvest fresh fruit market. The variety has moderate plant vigor, upright growth habit, ripens mid-season, and produces very large, uniform fruit. 'FC13-122' was selected for its above average fruit quality compared to other mid-season varieties. The fruit is larger and firmer than any standard commercial variety in the same harvest window.

'FC13-122' has a more upright growth habit compared to the parents 'ZF06-050' (not patented) and 'ZF06-013' (not patented) that have a semi-sprawling growth habit. 'FC13-122' differs from the female parent 'ZF06-050' (not patented) in that it has moderate vigor and larger fruit where 'ZF06-050' (not patented) has low vigor and smaller fruit. 'FC13-122' differs from the male parent 'ZF06-013' (not patented) in that it has a higher yield and larger, firmer fruit.

Pedigree and History: The new blueberry plant originated from a cross of 'ZF06-050' (female parent, not patented) and 'ZF06-013' (male parent, not patented) made in Lowell, Oreg., USA in 2010 and was selected in the same location in 2013.

The new blueberry variety 'FC13-122' was initially propagated by softwood cuttings in 2013 from the original seedling in Lowell, Oreg., USA and planted in a replicated plot of nine plants in fall 2014. The plants established in Oregon were successfully used to establish in vitro culture lines in 2017.

'FC13-122' was selected in 2013 because of its high-quality fruit—firm, crisp, light blue color, and very large size. After two additional years of evaluation in Lowell, Oreg., 'FC13-122' was determined to be sufficiently cold hardy and adaptable to commercial management strategies, and have a competitive yield for the harvest season. Plants of 'FC13-122' propagated from softwood cuttings or in vitro are phenotypically stable and exhibit the same characteristics as the original plant.

SUMMARY OF THE INVENTION

The new blueberry plant variety 'FC13-122' has not been observed under all possible environmental conditions. The phenotype may vary somewhat with variations in environment and cultural practices such as temperature and light intensity without, however, any variance in genotype.

'FC13-122' is distinguished by an upright growth habit, moderate vigor, very large fruit, high number of berries per cluster, and long inflorescence. The following characteristics of the new cultivar have been repeatedly observed and are determined to be the unique characteristics of the new blueberry plant variety 'FC13-122':

1) Mid-season ripening
2) Very large, uniform fruit size
3) Firm fruit texture
4) Excellent long-term cold storage performance

BRIEF DESCRIPTION OF THE DRAWINGS

The accompanying photographic illustration shows typical specimens in full color of the foliage and fruit of the new variety 'FC13-122.' The colors are as nearly true as is reasonably possible in a color representation of this type.

Figure 1:
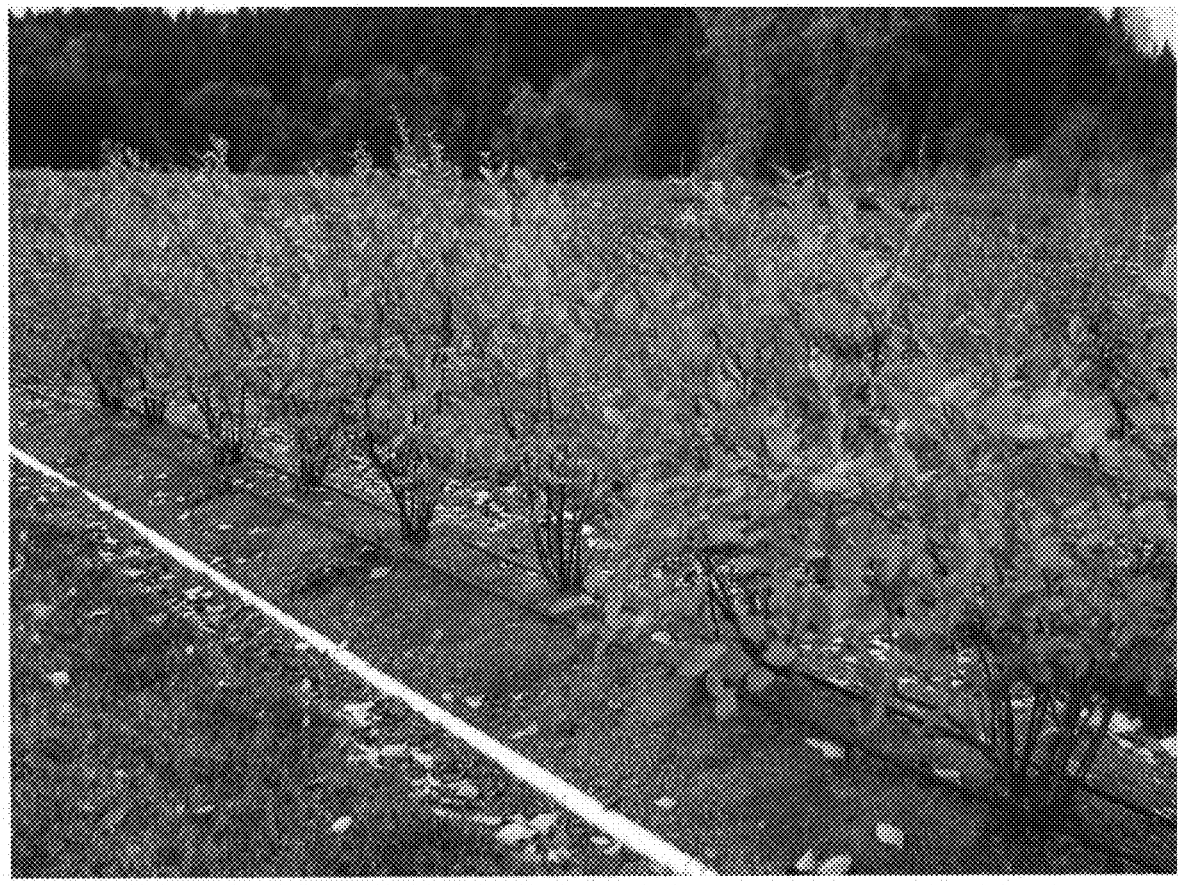
FIG. 1 is a photograph of the new variety 'FC13-122', demonstrating the plant's leaves and growth habit in the fall. The plants were grown in Lowell, Oreg. and photographed on Nov. 15, 2017.
Figure 2:
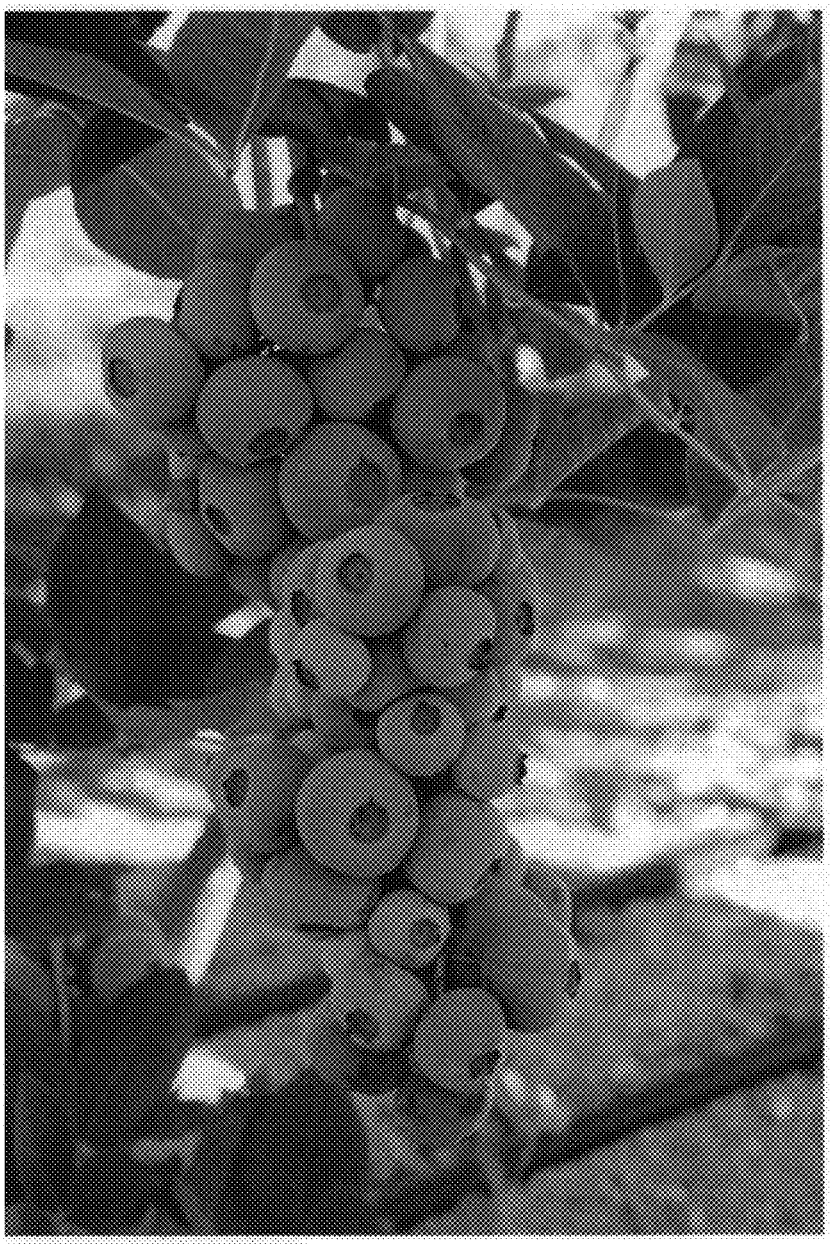
FIG. 2 is a photograph of the fruit cluster of the new variety 'FC13-122' grown in Lowell, Oreg. and photographed on Jul. 19, 2017.
Figure 3:
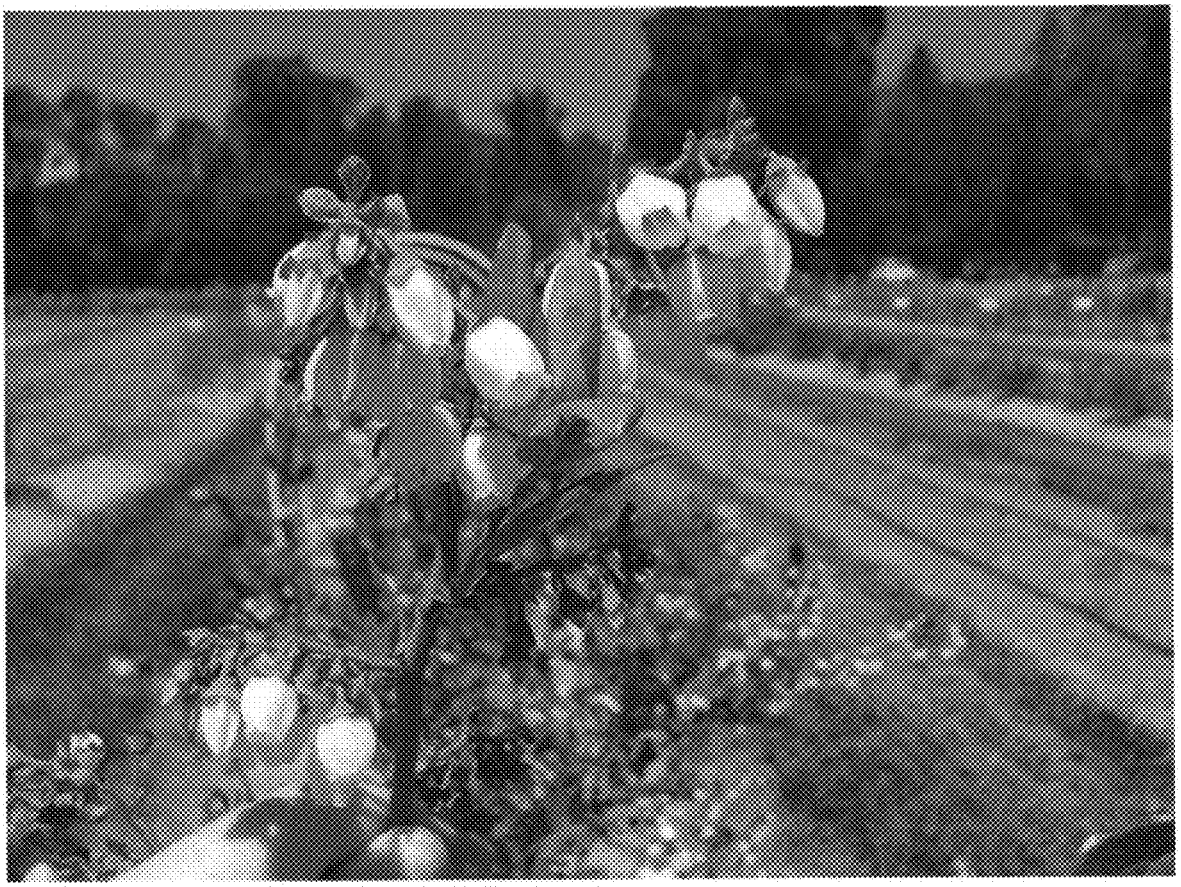
FIG. 3 is a photograph of the flowers of the new variety 'FC13-122' grown in Lowell, Oreg. and photographed on May 18, 2017.
Figure 4:
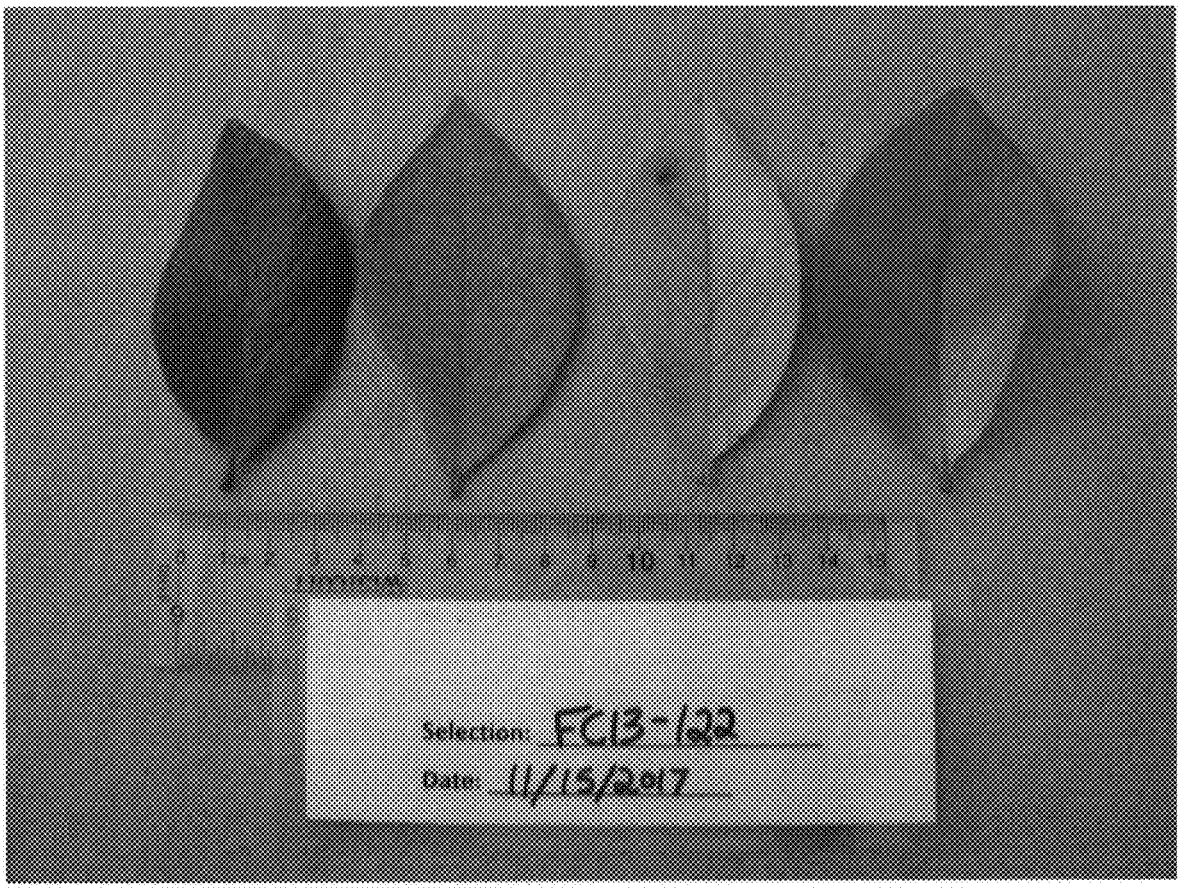
FIG. 4 is a photograph of the fall foliage of the new variety 'FC13-122' grown in Lowell, Oreg. and photographed on Nov. 15, 2017.
Figure 5:
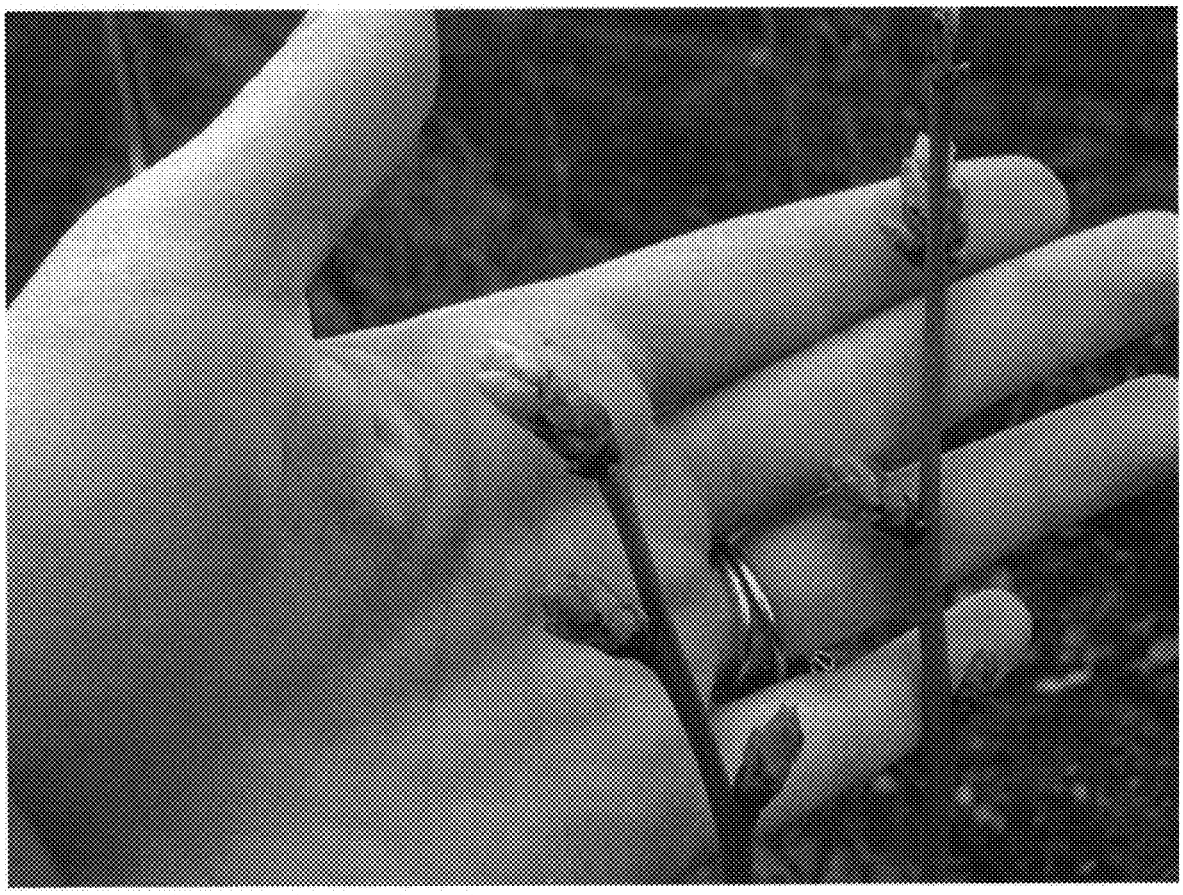
FIG. 5 is a photograph of early buds on the new variety 'FC13-122' grown in Lowell, Oreg. and photographed on Mar. 16, 2017.
Figure 6:
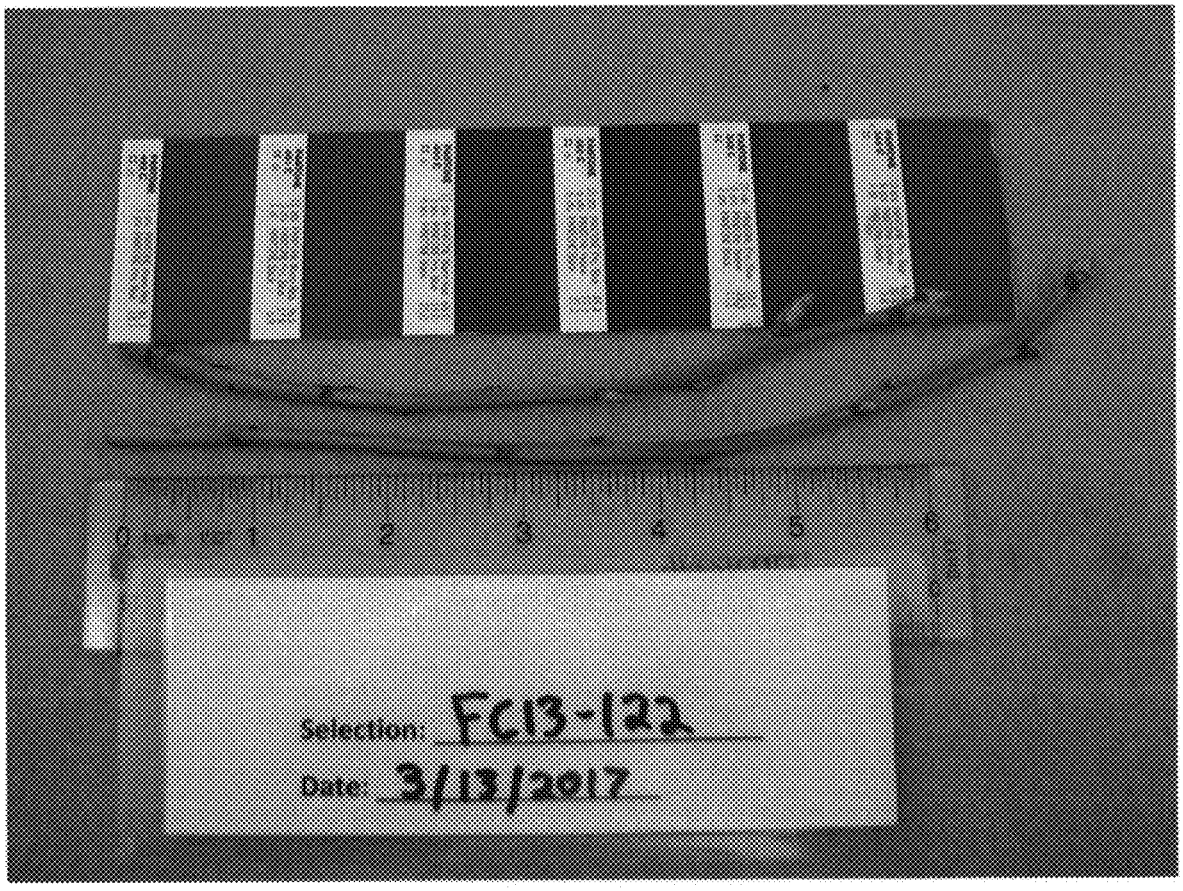
FIG. 6 is a photograph of one year old canes on the new variety 'FC13-122' grown in Lowell, Oreg. and photographed on Mar. 13, 2017.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FC13-122'. The data that define these characteristics were collected from asexual reproductions of the original selection. Dimensions, sizes, colors, and other characteristics are approximations and averages set forth as accurately as possible. The plant history was taken on plants approximately 3 years of age, and the descriptions relate to plants grown in the field located at 39252 Jasper-Lowell Road, Lowell, Oreg., USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

Classification:

a. *Family*.—Ericaceae.
b. *Genus*.—*Vaccinium*.
c. *Species*.—*corymbosum*.
d. *Common name*.—Northern Highbush Blueberry.

Parentage: Female Parent—'ZF06-050.' (unpatented). Male Parent—'ZF06-013.' (unpatented).

Market class: Hand harvest fresh market.

PLANT

General:

a. *Parentage*.—Female Parent — 'ZF06-050' (unpatented). Male Parent — 'ZF06-013' (unpatented).
b. *Plant height*.—Average 1.24 m.
c. *Plant width*.—Average 1.34 m.
d. *Growth habit*.—Upright.
e. *Growth*.—Moderate vigor.
f. *Productivity*.—High. In Lowell, Oreg. on 2 year old plants 3.15 lbs. per plant, compared to Draper plants of the same age which produced an average of 4.10 lbs. per plant. On 3 year old plants 'FC13-122' produced 5.59 lbs. per plant, compared to Draper that produced an average of 5.18 lbs. per plant.
g. *Cold hardiness*.—Approximately USDA zones 6-8 but tested to only USDA zone 8.
h. *Chilling requirement*.—Estimated minimum of 500-1000 hours below 45 degrees Fahrenheit.
i. *Leafing*.—Moderate.
j. *Twigginess*.—Not twiggy.
k. *Resistance/susceptibility to root rot* (*Phytopthora cinnamomii*).—Does not seem overly susceptible.
l. *Resistance/susceptibility to stem blight* (*Botryosphaeria* sp.).—Does not seem overly susceptible.
m. *Resistance/susceptibility to phomopsis twig blight* (*Phomopsis vaccinii*).—Does not seem overly susceptible.
n. *Resistance/susceptibility to Botrytis* (*Botrytis cinerea*).—Does not seem overly susceptible.
o. *Resistance/susceptibility to leaf spot* (*Septoria* spp.) .—Does not seem overly susceptible.
p. *Resistance/susceptibility to leaf rust* (*Naohidemyces vaccinii*).—Does not seem overly susceptible.
q. *Resistance/susceptibility to bud mites* (*Acalatus vaccinii*).—Undetermined.

STEM

General:

a. *Suckering tendency*.—None.
b. *Mature cane color*.—Pantone color Brush 16-1317.
c. *Mature cane length*.—Average 1.08 m.
d. *Mature cane width*.—Average 1.21 cm.
e. *Bark texture*.—Rough.
f. *Fall color on new shoots*.—Pantone color Grasshopper 18-0332.
g. *Surface texture of new wood*.—Smooth.
h. *Internode length on strong, new shoots*.—41.35 mm.
i. *Average number of buds per fruiting lateral*.—12.4.

FOLIAGE

General:

a. *Time of beginning of leaf bud burst*.—In Lowell, Oreg., mid March to early April.
b. *Leaf color* (*top side*).—Pantone color Chive 19-0323.
c. *Leaf color* (*under side*).—Pantone color Sage Green 15-0318.
d. *Leaf arrangement*.—Alternate.
e. *Leaf shape*.—Broadly elliptic.
f. *Leaf margins*.—Entire.
g. *Undulation of margin*.—None.
h. *Leaf venation*.—Anastomosing.
i. *Leaf apices*.—Acute/Attenuate.

j. *Leaf bases*.—Obtuse.
k. *Leaf Length*.—Average 77.25 mm.
l. *Leaf Width*.—Average 45.75 mm.
m. *Leaf length/width ratio*.—1.69 — medium.
n. *Leaf nectarines*.—Absent.
o. *Pubescence of upper side*.—None.
p. *Pubescence of lower side*.—None.
q. *Cross sectional profile*.—Flat.
r. *Longitudinal profile*.—Plane.
s. *Attitude*.—Porrect.
t. *Fall leaf color*.—Pantone color Fiery Red 18-1664 and Pantone color Spectra Yellow 14-0957.

Petioles:
a. *Length*.—Average 4.34 mm.
b. *Width*.—Average 2.15 mm.
c. *Color*.—Pantone color Green Oasis 15-0538.
d. *Petiole surface texture*.—Smooth.

FLOWERS

General:
a. *Time of beginning of flowering*.—Approximately mid to late April in Lowell, Oreg.
b. *Time of* 50% *anthesis*.—Approximately early May in Lowell, Oreg.
c. *Flower shape*.—Urceolate.
d. *Flower bud density*.—Medium.
e. *Flower fragrance*.—Faint floral scent.
f. *Immature flower color*.—Pantone color Pastel Parchment 11-0603.
g. *Self-compatibility*.—Very good. Approximately 71% of self-pollinated flowers reached maturity on self-compatibility pollination trials, compared to 81% of flowers reached maturity when pollinated with pollen of the variety 'Liberty' (U.S. Plant Pat. No. 15,146).

Corolla:
a. *Color*.—Pantone color Pastel Parchment 11-0603.
b. *Length*.—8.22 mm.
c. *Width*.—8.61 mm.
d. *Aperture width*.—4.54 mm.
e. *Anthocyanin coloration of corolla*.—None.
f. *Corolla ridges*.—Present.
g. *Protrusion of stigma*.—Does not protrude — average 0.49 mm. below the corolla.

Inflorescence:
a. *Length*.—44.35 mm.
b. *Diameter*.—41.78 mm.
c. *Length of peduncle*.—36.13 mm.
d. *Surface texture of peduncle*.—Smooth.
e. *Color of peduncle*.—Pantone color Faded Rose 18-1629.
f. *Length of pedicel*.—8.88 mm.
g. *Surface texture of pedicel*.—Smooth.
h. *Color of pedicel*.—Pantone color Faded Rose 18-1629.
i. *Number of flowers per cluster*.—11.2.
j. *Flower cluster density*.—Medium loose.

Calyx (with sepals):
a. *Diameter*.—8.63 mm.
b. *Color* (*sepals*).—Pantone color Jade Lime 14-0232.

Stamen:
a. *Length*.—6.30 mm.
b. *Number per flower*.—Average 10.33 stamen per flower.
c. *Filament color*.—Pantone color Citron 12-0524.

Pistil:
a. *Length*.—10.80 mm.
b. *Ovary color* (*exterior*).—Pantone color Peridot 17-0336.
c. *Style length*.—8.24 mm.

Anther:
a. *Length*.—3.74 mm.
b. *Number*.—2 anthers per stamen.
c. *Color*.—Pantone color Bright Gold 16-0947.

Pollen:
a. *Abundance*.—Moderate.
b. *Color*.—Pantone color Cornhusk 12-0817.

FRUIT

General:
a. *Time of fruit ripening*.—Mid season in Lowell, Oreg.
b. *Time of* 50% *maturity*.—Approximately the middle of July in Lowell, Oreg.
c. *Fruit development period*.—70 days in Lowell, Oreg. in 2017.
d. *Mean harvest date*.—July 20.
e. *Mean date last pick*.—August 1.
f. *Cluster density*.—Medium to medium loose.
g. *Berries per cluster*.—9.4 berries per cluster.
h. *Unripe fruit color*.—Pantone color Spinach Green 16-0439.
i. *Ripe Berry color*.—Pantone color Dapple Grey 16-3907.
j. *Berry skin color after polishing*.—Pantone Color Ebony 19-4104.
k. *Berry surface wax abundance*.—Medium.
l. *Berry flesh color*.—Pantone color Hay 12-0418.
m. *Berry weight*.—Average 3.72 g.
n. *Berry height from calyx to scar*.—14.20 mm.
o. *Berry diameter*.—21.82 mm.
p. *Calyx aperture*.—Average 7.40 mm.
q. *Calyx depth*.—Average 1.09 mm.
r. *Pedicel length*.—Average 10.81 mm.
s. *Pedicel surface texture*.—Smooth.
t. *Berry detachment force*.—Medium-strong.
u. *Berry shape*.—Oblate.
v. *Fruit stem scar*.—Medium, dry.
w. *Sweetness when ripe*.—Medium.
x. *Firmness when ripe*.—High.
y. *Acidity when ripe*.—Low.
z. *Storage quality*.—Excellent.

SEED

General:
a. *Seed abundance in fruit*.—Moderate.
b. *Seed color*.—Pantone color Aztec 18-1130.
c. *Seed dry weight*.—0.27 mg. per seed.
d. *Seed length*.—Average 1.65 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety 'FC13-122' |
|---|---|---|---|
| Draper (U.S. Plant Pat. No. PP15,103) | Fruit size | Large (18 mm/2.4 g) | Very large (22 mm/3.7 g) |
| Draper | Bloom retention | Poor | Moderate |
| Legacy (not patented) | Fruit size | Large (17 mm/2.2 g) | Very large (22 mm/3.7 g) |
| Legacy | Firmness | Firm (233 g/mm) | Very firm (364 g/mm) |

TABLE 1-continued

Comparison Table

| Denomination of similar variety | Characteristic for comparison | State of expression of similar variety | State of expression of candidate variety 'FC13-122' |
|---|---|---|---|
| ZF06-050 (not patented) | Vigor | Low | Moderate |
| ZF06-013 (not patented) | Growth habit | Semi-sprawl | Upright |

The invention claimed is:

1. A new and distinct variety of blueberry plant named 'FC13-122', substantially as illustrated and described herein.

* * * * *